(12) United States Patent
McCarthy

(10) Patent No.: US 8,360,772 B1
(45) Date of Patent: Jan. 29, 2013

(54) DUAL ARCH ADJUSTABLE DENTAL IMPRESSION TRAY

(76) Inventor: Evan McCarthy, Brookfield, WI (US)

( * ) Notice: Subject to any disclaimer, the term of this patent is extended or adjusted under 35 U.S.C. 154(b) by 0 days.

(21) Appl. No.: 13/312,943

(22) Filed: Dec. 6, 2011

(51) Int. Cl.
*A61C 9/00* (2006.01)
(52) U.S. Cl. .................................................. 433/41
(58) Field of Classification Search ........... 433/37, 433/41, 42, 43, 45
See application file for complete search history.

(56) References Cited

U.S. PATENT DOCUMENTS

| | | | | |
|---|---|---|---|---|
| 1,054,999 | A | * | 3/1913 | Thein .............................. 433/41 |
| 1,652,910 | A | * | 12/1927 | Psayla ............................. 433/41 |
| 2,860,414 | A | * | 11/1958 | Brant .............................. 433/43 |
| 4,003,132 | A | * | 1/1977 | Beck .............................. 433/42 |
| 6,428,315 | B1 | * | 8/2002 | Prestipino et al. .............. 433/45 |
| 6,629,841 | B1 | | 10/2003 | Skinner |
| 7,270,540 | B2 | | 9/2007 | Skinner |
| 2004/0009451 | A1 | | 1/2004 | Skinner |
| 2008/0311536 | A1 | | 12/2008 | Kim et al. |

* cited by examiner

*Primary Examiner* — Ralph Lewis
(74) *Attorney, Agent, or Firm* — Absolute Technology Law Group LLC

(57) ABSTRACT

The present invention relates to an adjustable dual arch dental impression tray which accommodates a wide range of upper and lower individual arch sizes.

20 Claims, 9 Drawing Sheets

DUAL ARCH ADJUSTABLE DENTAL IMPRESSION TRAY

FIELD OF INVENTION

The present invention relates to the field of dental impression devices, and more specifically to a dual arch dental impression tray which may be used for both the upper and lower dentition.

GLOSSARY

Figure 1:
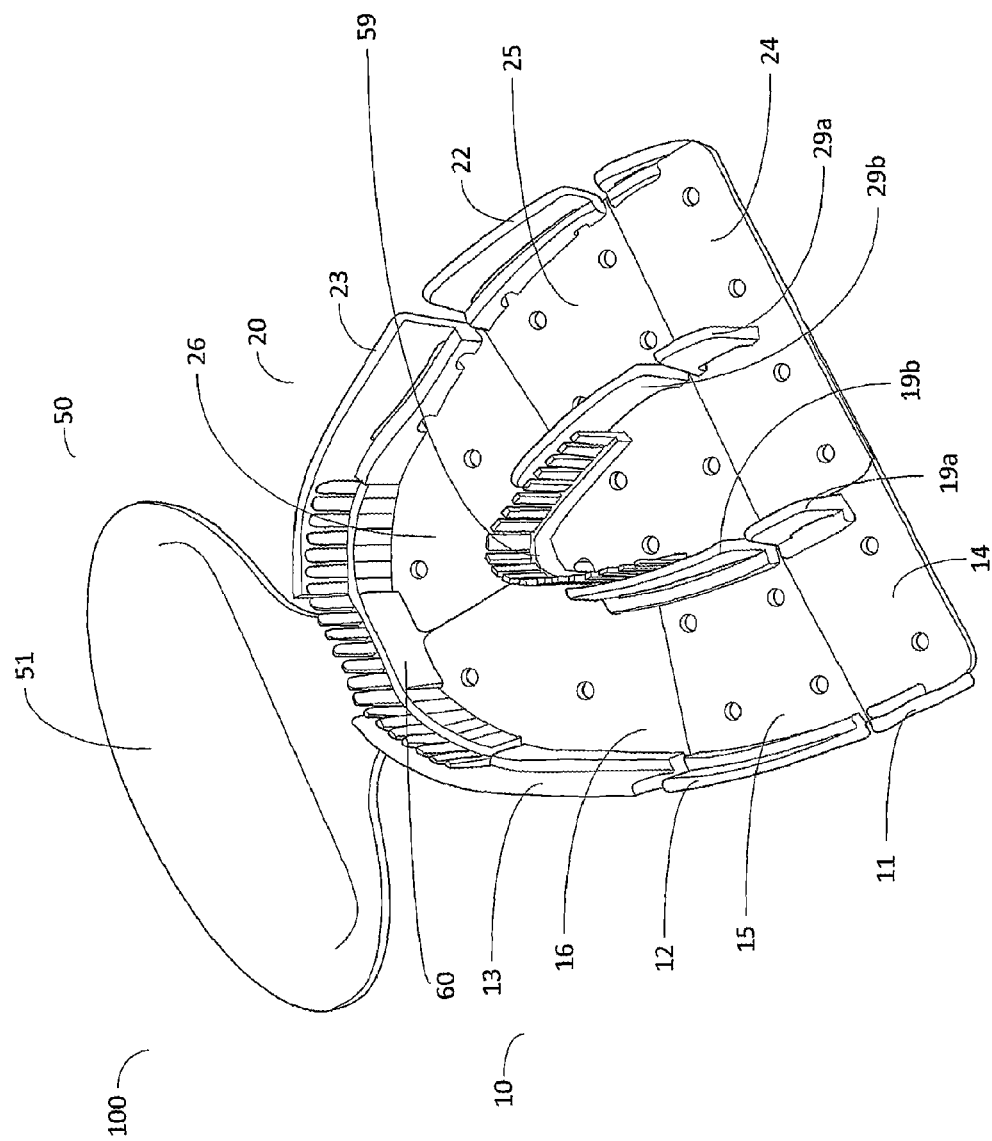
FIG. 1 is a top perspective view of an exemplary embodiment of a dual arch dental impression tray comprised of three component plates.

As used herein, the term "adherence aperture" refers to any opening, hole, slit, crack, or gap in a dental impression tray which is adapated to capture a portion of impression material in order to secure the impression material in place.

As used herein, the term "base member" refers to a plate which is curved and to which other components of a dual arch dental impression tray are mounted, and which is and adapated to fit into the mouth. A base component may be rigid, semi-rigid or flexible. A base member may be comprised of one or more selectively attachable plate components.

As used herein; the term "breaking plane" refers to an area which is structurally formed to facilitate breaking or separation of the component into two or more parts. For example, a breaking plane may be a groove, thinned area or a serrated or pieced area to alter the overall size of the component without changing its functionally.

As used herein, the term "breakaway cylindrical component" refers to cylindrical components which have a breaking plane for shortening or removal.

As used herein, the term "dual arch" or "dental impression tray" refers to a device or dental impression tray capable of being used to receive impressions of the upper and/or lower arches.

As used here, the term "flexible flap member" means a component made from more flexible material than a base component.

As used herein, the term "gripping member" refers to any extending component (e.g., a handle or lever) which may gripped or manually adjusted or manipulated.

As used herein, the term "half-plate" refers to one of two components of dental impression tray which are cojoined to form a dual arch dental impression tray.

As used herein, the term "impression material" refers any material capable of creating a reproduction of teeth, dental or arch characteristics. Impression material may include but is not limited to alginate, polyether and silicones (both condensation-cured silicones and addition-cured silicones, such as polyvinyl siloxane) and combinations and functional equivalents of the foregoing.

As used herein, the term "inner-bite guard member" refers to a protruding inner rim section on a dental impression tray which creates a barrier between the teeth and the tongue and is further adapted to contain impression material in a dental impression tray.

As used herein, the term "lower arch" refers to the plurality of lower dentition, supporting tissue and arch of the lower jaw.

As used herein, the term "lower dentition" refers to the plurality of lower teeth.

As used herein, the term "outer-bite guard" refers to a protruding rim section on a dental impression tray which creates a barrier between the teeth and the lip of a mouth and is further adapted to contain impression material in a dental impression tray.

As used herein, the term "seam" means any surface at which two structures are adapted to be joined or interface.

As used herein, the term "upper arch" refers to the plurality of upper dentition, supporting tissue and arch of the upper dentition.

As used herein, the term "upper dentition" refers to the plurality of upper teeth.

As used herein, the term "upper palate" refers to the roof of the mouth, the frenum, the buccal, the plurality of upper dentition, and the arch of the upper teeth.

BACKGROUND

Dental impression trays are used create a negative imprint of the teeth and surrounding tissue, which can then be used to make a cast or 'positive' model of the dentition. This cast may be used for the fabrication of dentures, crowns, removal dental devices, or other prostheses and orthodontics.

In order to create the most effective and accurate impression, the entire dental arch and supporting tissue should be included in the mold. However, in order to accommodate all mouth sizes, a plurality of different sized impression trays are required. Currently there are four standard sizes of dental impression trays. This process can become very inefficient when a user does not know which size impression tray is needed to accommodate his/her mouth. Historically, two separate styles of dental trays may be required, one for the upper arch and one for the lower arch. The lower tray is typically designed to accommodate tongue presence, while the upper tray is designed for palatal coverage. Therefore a need exists for a single adjustable dental impression tray which can comfortably accommodate a wide variety of either the upper or lower arch forms.

It is known in the art to have an adjustable dental impression tray with two halves connected by a front pivoting member as disclosed in Skinner (U.S. Pat. No. 7,270,540). Skinner teaches an impression tray comprised of two overlapping halves which are connected in the front by a pivoting member. However, as the two halves are opened, to accommodate a wider mouth, a large gap is created in the front of the impression tray where the impression material extrudes. Additionally, when separating the two dental impression halves by a pivoting member in the front, the natural arc of the dental tray rim is destroyed and will decrease effectiveness of the impression.

A disadvantage of existing non-adjustable trays is that they require multiple standard sizes. Additionally, an upper palate tray and a separate lower arch tray are needed to accommodate the arches. This results in waste of time while selecting the correct tray size, and a waste of storage space required to store the plurality of trays.

Further, another disadvantages of existing adjustable trays is that the arc created by the pivoting motion distorts the natural arc need to achieve an accurate impression. Additionally, as the two halves the dental tray are expanded, a large gap is created in the front rim of the tray and impression material extrudes out when pressure is applied.

Therefore, a need exists for a universal dental impression tray that can comfortably and accurately accommodate all mouth sizes. Moreover, a need exists for a dental tray which can be used for both the upper and/or lower arch.

SUMMARY OF THE INVENTION

The present invention is a dual arch adjustable dental impression tray comprised of a two rigid opposing half-plates which move laterally and include a plurality of detachable sections to accommodate different size mouths. The first and second rigid opposing half-plates have a base member and at least three detachable outer-bite guard members positioned parallel to at least two detachable inner-bite guard members. The present invention includes at least one flexible flap member which spans between the front detachable outer-bite guard members on each of the opposing half-plates. The dental impression tray further includes a flat oval shaped gripping member.

The first and second rigid opposing half-plates combine together to form a single adjustable arch conforming plate. The base members of first and second opposing half-plates include a series of breakaway seams which allow sections of the plate to be removed to accommodate different sized mouths.

DETAILED DESCRIPTION OF INVENTION

For the purpose of promoting an understanding of the present invention, references are made in the text to exemplary embodiments of a dual arch dental impression tray, only some of which are described herein. It should be understood that no limitations on the scope of the invention are intended by describing these exemplary embodiments. One of ordinary skill in the art will readily appreciate that alternate but functionally equivalent dual arch dental impression tray may be used. The inclusion of additional elements may be deemed readily apparent and obvious to one of ordinary skill in the art. Specific elements disclosed herein are not to be interpreted as limiting, but rather as a basis for the claims and as a representative basis for teaching one of ordinary skill in the art to employ the present invention.

It should be understood that the drawings are not necessarily to scale; instead emphasis has been placed upon illustrating the principles of the invention. In addition, in the embodiments depicted herein, like reference numerals in the various drawings refer to identical or near identical structural elements.

Moreover, the terms "substantially" or "approximately" as used herein may be applied to modify any quantitative representation that could permissibly vary without resulting in a change in the basic function to which it is related.

FIG. 1 illustrates an exemplary embodiment of adjustable dual arch dental impression tray 100 comprised of first rigid opposing half-plate 10, second rigid opposing half-plate 20, and center plate 50. First rigid opposing half-plate 10 and second rigid opposing half-plate 20 are attached to center plate 50 and movable in a lateral direction to accommodate a wider mouth. Dual arch dental impression tray 100 consists of a channel for receiving teeth which is defined by a base member and an inner and outer-bite guard member which are used to contain impression material.

In the embodiment shown, dental impression tray 100 includes a series of detachable outer-bite guard members which fit between the teeth and lips. In the embodiment shown, first rigid opposing half-plate 10 has rear detachable outer-bite guard member 11, middle detachable outer-bite guard member 12, and frontal detachable outer-bite guard member 13. Similarly, in the embodiment shown, second rigid opposing half-plate 20 has rear detachable outer-bite guard member 21, middle detachable outer-bite guard member 22, and frontal detachable outer-bite guard member 23. In other embodiments, dental impression tray 100 may include more or less individual detachable outer-bite guard members.

In the embodiment shown, the top half of detachable outer-bite guard members may be removed to accommodate a mouth which has a lower gum line. In the embodiment shown, detachable outer-bite guard members 11, 12, 13, 21, 22, and 23 include seams, which create a breaking plane, and therefore the top section of detachable outer-bite guard members may be broken off and removed to form a quasi-unique and anthropometrically contoured mouthpiece, adapted to the physical characteristics of an individual.

In the embodiment shown, the base member of first rigid opposing half-plate 10 consists of rear breakaway section 14, forward breakaway section 15, and base surface 16. Similarly, the base member of second rigid opposing half-plate 20 consists of rear breakaway section 24, forward breakaway section 25, and base surface 26. Rear and forward breakaway sections are defined by seams where the sections may be removed to accommodate a smaller or shallower mouth. In the embodiment shown, first rigid opposing plate 10 has rear and forward detachable inner-bite guard members 19a and 19b while second rigid opposing plate 20 has matching rear and forward detachable inner-bite guard members 29a and 29b. Detachable inner bite-guard members 19a, 19b, 29a and 29b are used to contain the impression material within the teeth receiving channel. In the embodiment shown, the detachable inner-bite guard members also include seams where the top portion may be removed to accommodate a shallower mouth.

In the embodiment shown, center plate 50 has front flexible flap member 60 which is perpendicular to the teeth receiving channel and is adapted to curve inside frontal detachable outer-bite guard members 13 and 23. Front flexible flap member 60 includes a plurality of vertically aligned cylindrical components which may be removed to accommodate a user's frenum, or tissue between the gum and lip. Front flexible flap member 60 prevents impression material from extruding through the front of the dental tray as the two rigid opposing half-plates are spread apart to accommodate wider mouths. In the embodiment shown, as first rigid opposing half-plate 10 and second rigid opposing half-plate 20 are separated laterally, front flexible flap member 60 flexes to maintain a consistent arc in the front of dental impression tray 100.

In the embodiment shown, center plate 50 also has rear flexible flap member 65 which is adapted to curve inside forward inner-bite guard members 19b and 29b. Similarly, as first rigid opposing half-plate 10 and second rigid opposing half-plate 20 are separated to accommodate a larger mouth, a consistent and closed channel is formed in the base member of each half-plate.

In the embodiment shown, detachable outer-bite guard members include a ridge which corresponds to a ridge on front flexible flap member 60. The ridge ensures that when a downward pressure is applied on gripping member 51, all three components of dental impression tray 100 remain together.

Figure 2:
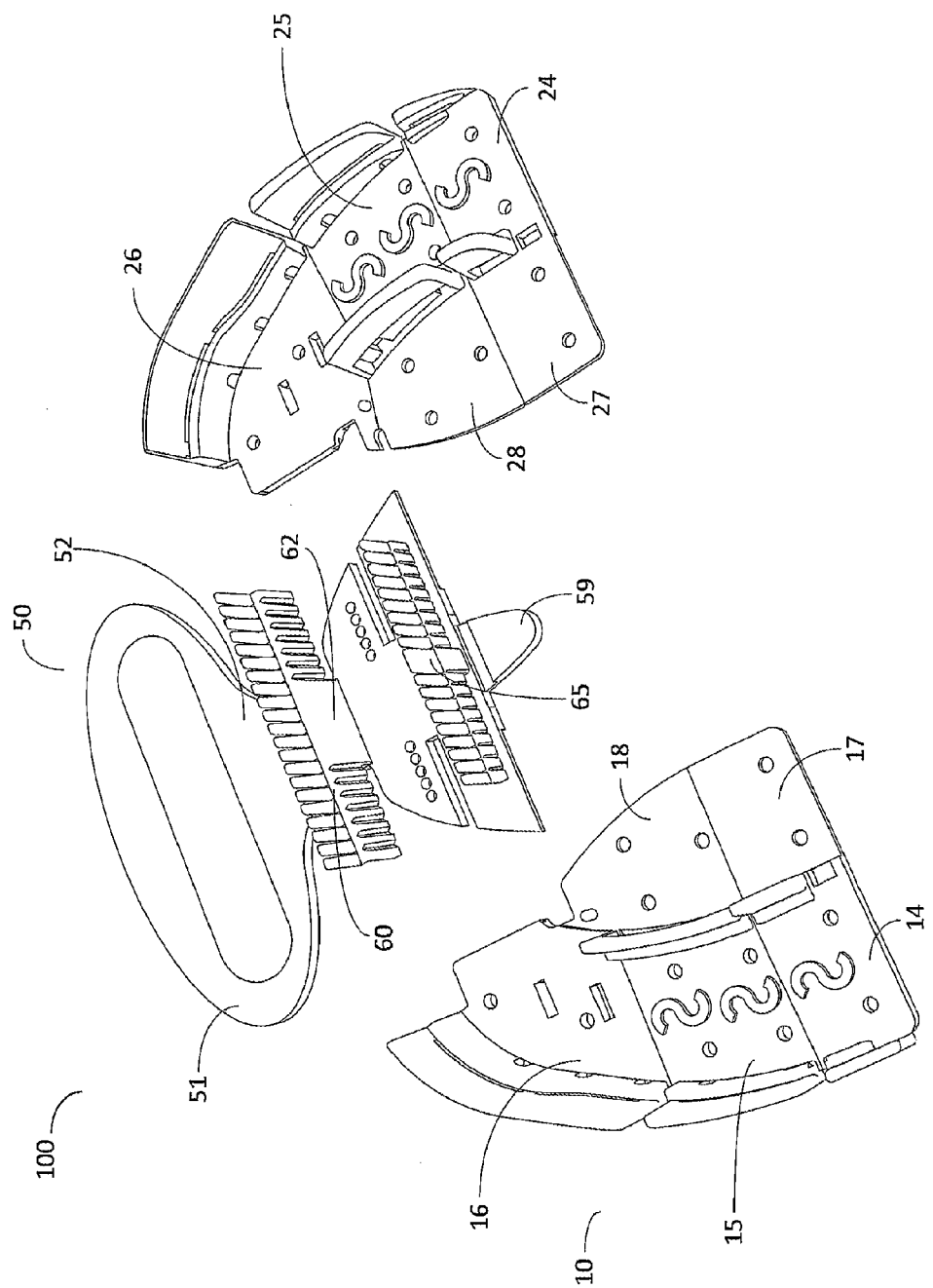
FIG. 2 is an exploded perspective view of an exemplary embodiment of a dual arch dental impression tray comprised of three component plates.

FIG. 2 illustrates an exploded perspective view of dual arch adjustable dental impression tray 100 comprised of first rigid opposing half-plate 10, second rigid opposing half-plate 20, and center plate 50. In the embodiment shown, center plate 50 is comprised of gripping component 51 which is a flat oval shaped plate that may be used for holding while inserting and removing dental impression tray 100 or may be used for receiving identification indicia. Gripping component 51 is connected to front flexible flap member 60 by neck section 52. Front flexible flap member 60 is supported by upper center support member 62 and further includes a plurality of vertically aligned breakaway cylindrical components which may be removed to accommodate a user's frenum. In the embodiment shown, center plate 50 has rear flexible flap member 65 which also has a plurality of vertically aligned breakaway cylindrical components which may be removed to accommodate a shallower mouth. In the embodiment shown, center plate 50 also has peninsula shaped support structure 59 which supports tongue plate breakaway members.

In the embodiment shown, the teeth receiving channel on first rigid opposing half-plate 10 is comprised of rear breakaway section 14, forward breakaway section 15 and base surface 16. Similarly, the teeth receiving channel on second rigid opposing half-plate 20 is comprised of rear breakaway section 24, forward breakaway section 25 and base surface 26. Breakaway sections are defined by seams. In various embodiments, the teeth receiving channel may include more and or less breakaway seems.

In the embodiment shown, first rigid opposing plate 10 further includes rear tongue plate breakaway member 17 and forward tongue plate breakaway member 18. Second rigid opposing half-plate 20 includes rear tongue plate breakaway member 27 and forward tongue plate breakaway member 18. In other embodiments, first and second rigid opposing plates may include more or less plate breakaway members.

In the embodiment shown, first rigid opposing half-plate 10 and second rigid opposing half-plate 20 include a plurality of adherence apertures throughout the teeth receiving channel. Adherence apertures are adapted to capture a portion of the impression material in order to secure the impression material in place. In various embodiments, different shaped apertures or friction projections may be used. In the embodiment shown, an S-shaped pattern is projected from the teeth receiving channel.

Figure 3:
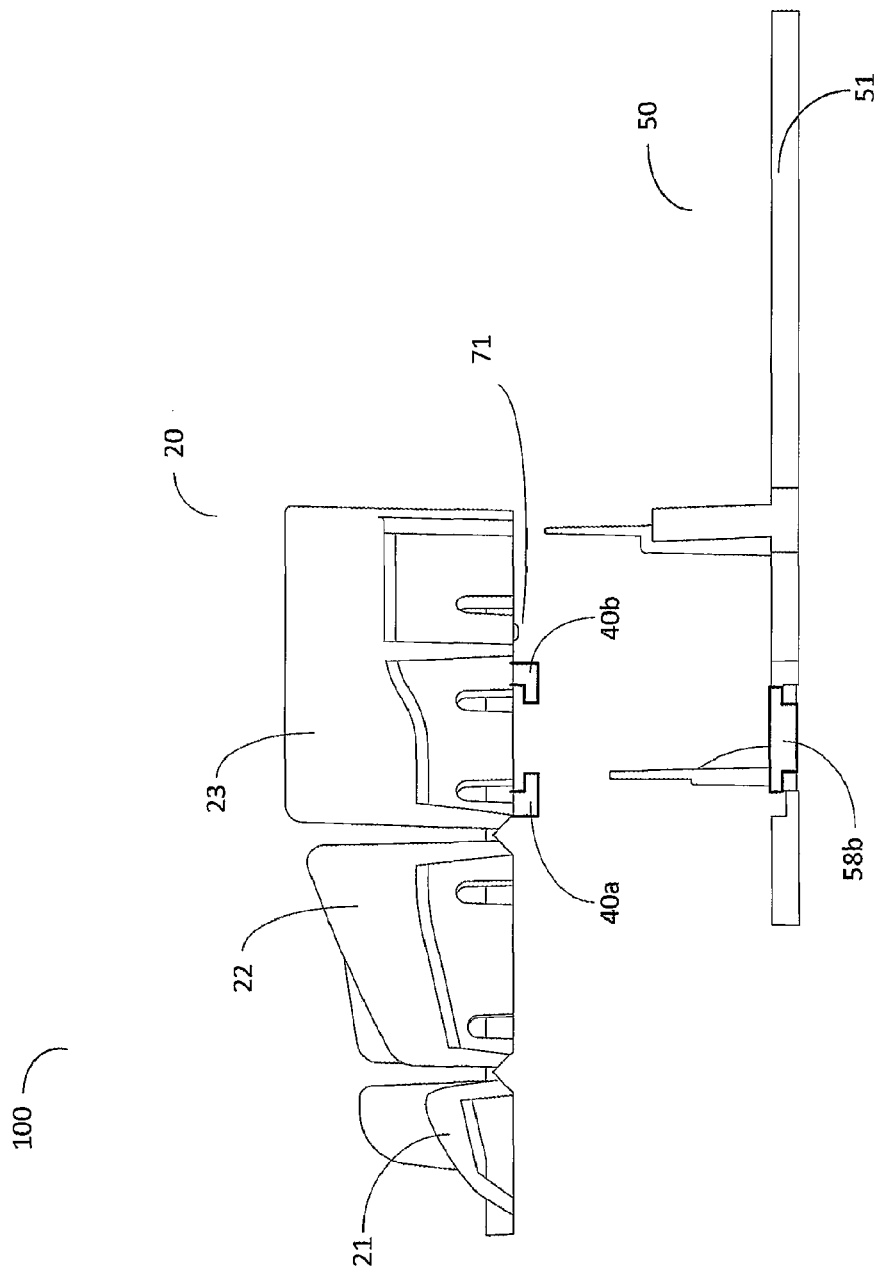
FIG. 3 is an exploded side view of an exemplary embodiment of a dual arch dental impression tray.

FIG. 3 is an exploded side view of an exemplary embodiment of adjustable dental impression tray 100 comprised of second rigid opposing half-plate 20 and center plate 50. First rigid opposing half-plate is a mirror of second rigid opposing half-plate and has been omitted for illustrative clarity. First rigid opposing half-plate 10 (not shown) has track support structures 30a and 30b (not shown) and second rigid opposing half-plate 20 has track support structures 40a and 40b. Track support structure 30a, 30b, 40a, and 40b are curved components used to engage a track system on center plate 50. In the embodiment shown, first rigid half-plate 10 (not shown) includes knob 70 (not shown), and second rigid opposing half-plate 20 has protrusion knob 71.

In the embodiment shown, center plate 50 has symmetrical track members 58a (not shown) and 58b which include ridges that correspond to the shape of track support structures. Track members 58a and 58b fit into track support structures and allow first rigid opposing half-plate 10 (not shown) and second rigid opposing half-plate 20 to separate laterally to accommodate a wider mouth.

In the embodiment shown, second rigid opposing half-plate 20 has rear detachable outer-bite guard member 21, middle detachable outer-bite guard member 22, and frontal detachable outer-bite guard member 23. Detachable outer-bite guard member include seams which allow a user to remove the top portion of detachable rim sections to accommodate a mouth with a lower gum line.

Figure 4:
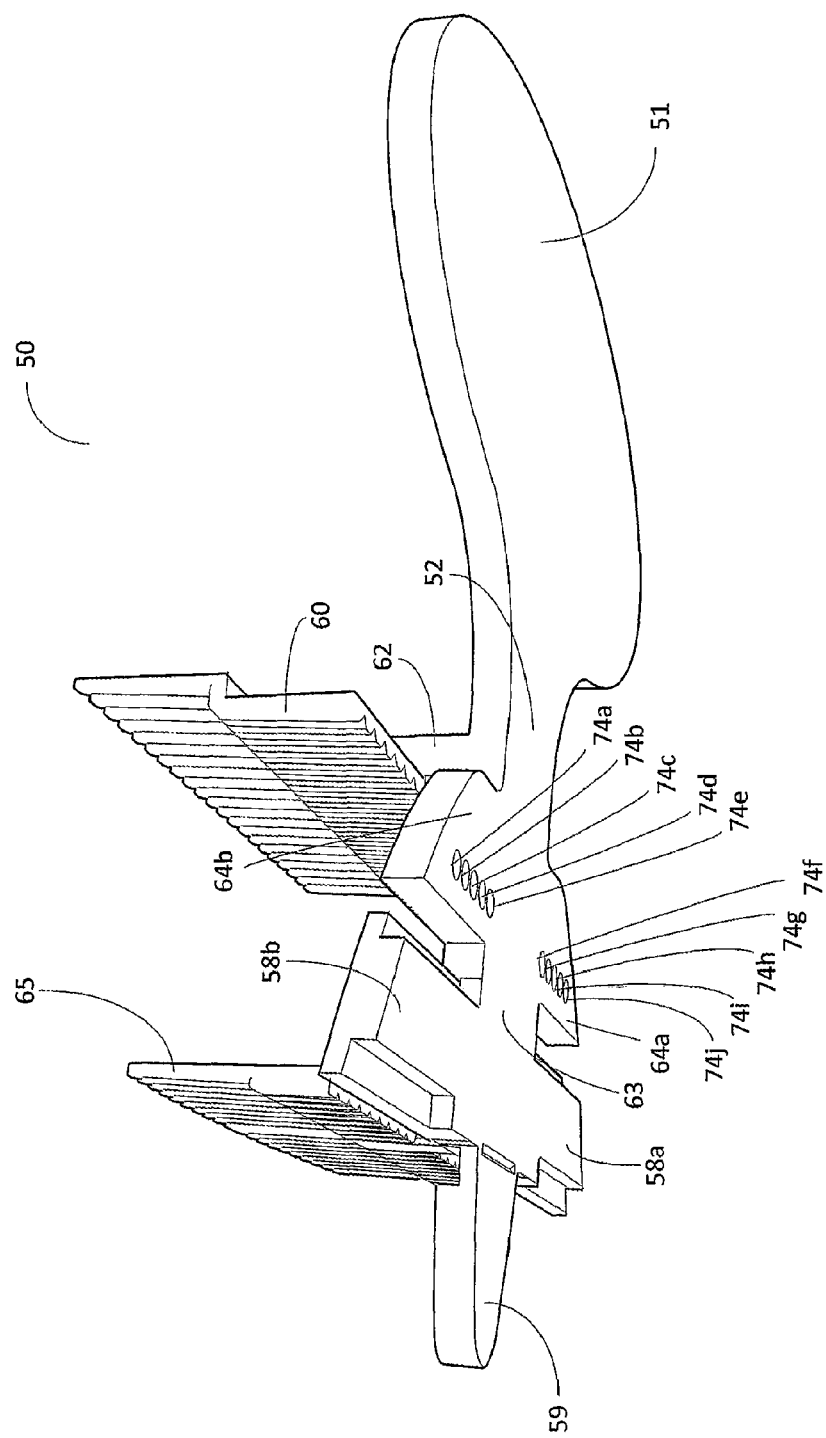
FIG. 4 is an isolated view of an exemplary embodiment of base plate component with track members.

FIG. 4 is an isolated view of an exemplary embodiment of center track component with track members. In the embodiment shown, center plate 50 is comprised of gripping member 51 which is connected to front flexible flap member 60 by neck section 52. Front flexible flap member 60 is supported by upper center support member 62 and further includes a plurality of vertically aligned breakaway cylindrical components which may be removed to accommodate a user's frenum. Center plate 50 also has rear flexible flap member 65 with a plurality of vertically aligned breakaway cylindrical components which may be removed to accommodate a mouth with a shallower palate. In the embodiment shown, center plate 50 includes peninsula shaped support structure 59 which supports tongue breakaway members (not shown).

In the embodiment shown, center plate 50 further includes side segments 64a and 64b which extend horizontally and further include apertures 74a, 74b, 74c, 74d, 74e, 74f, 74g, 74h, 74i and 74j. The bottom of first rigid opposing half-plate 10 and second rigid opposing plate 20 (shown in FIG. 2) each include knobs on the bottom of their respective base members which may fit into apertures 74a-j on side segments 64a and 64b. This allows first and second rigid opposing half-plates to move laterally and lock into place at small intervals, thus creating a plurality of different sized impression trays. In other embodiments, first and second rigid opposing half-plates may be secured to center plate by a ball and detent structure, interlocking tab members, flaps, snaps, contoured interlocking components, or other pressure components.

In the embodiment shown, center plate 50 further includes track members 58a and 58b which protrude horizontally out from attached center segment 63. In the embodiment shown, track members 58a and 58b have ridges which correspond to track support structures (shown in FIG. 3).

Figure 5:
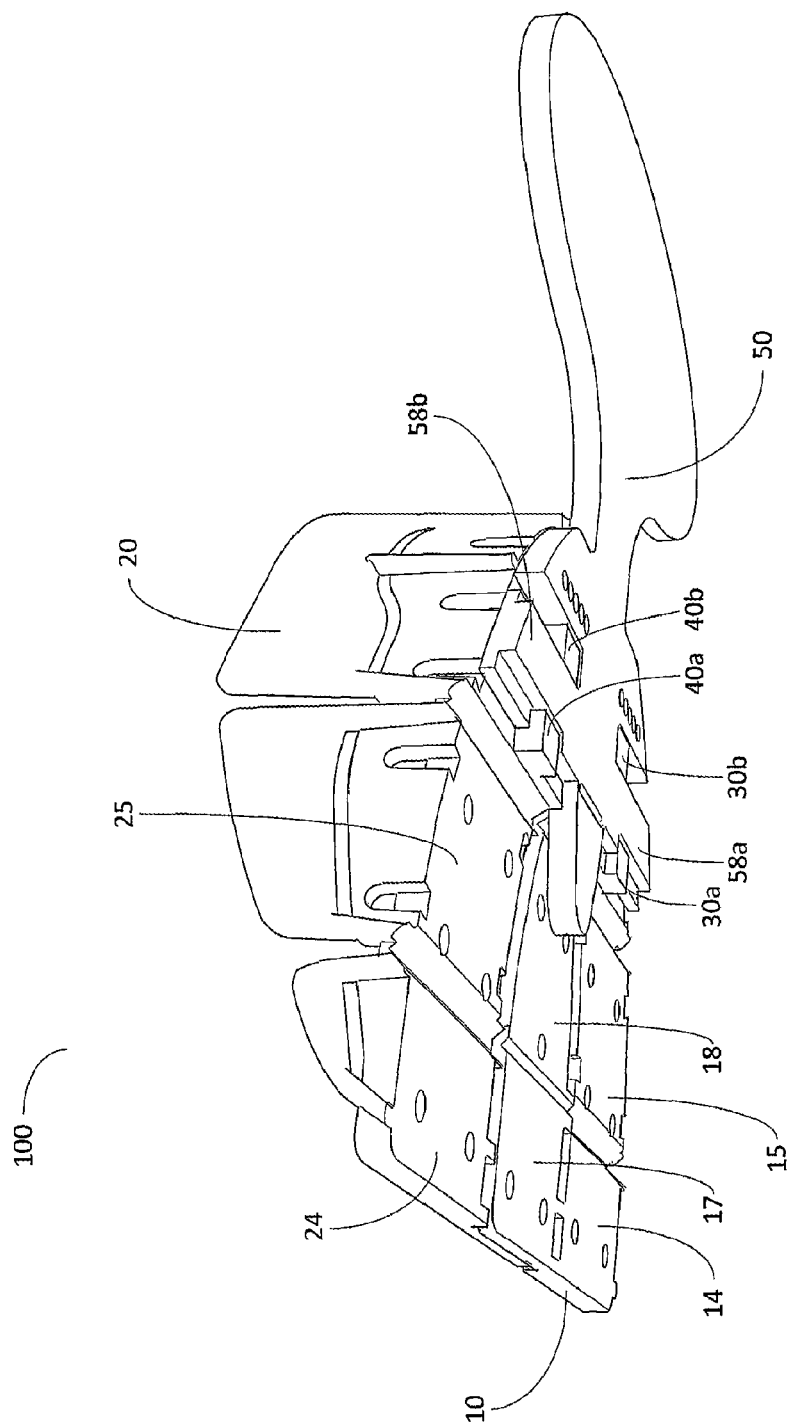
FIG. 5 is a bottom perspective view of an exemplary embodiment of three component dental impression tray.

FIG. 5 is a bottom perspective view of an exemplary embodiment of three component adjustable dental impression tray 100. In the embodiment shown, first rigid opposing half-plate 10 includes rear breakaway section 14 and forward breakaway section 15. Second rigid opposing plate includes rear break away section 24 and forward breakaway section 25. Breakaway sections 14, 15, 24 and 25 may be removed to create a shallower dental tray for users with small mouths. Further, in the embodiment shown, first rigid opposing half-plate 10 includes rear tongue plate breakaway member 17 and forward tongue plate breakaway member 18 which overlap corresponding tongue plate breakaway members on second rigid opposing half-plate 20. In various embodiments, first and second rigid opposing half-plates may include more or less tongue plate breakaway members.

In the embodiment shown, first rigid opposing half-plate 10 includes track support structures 30a and 30b while second rigid opposing half-plate 20 includes track support structures 40a and 40b which engage track members 58a and 58b on center plate 50. In the embodiment shown, track members 58a and 58b engage rigid opposing plates to create a solid dental impression tray and allow rigid opposing plates to move laterally to accommodate larger mouths.

Figure 6:
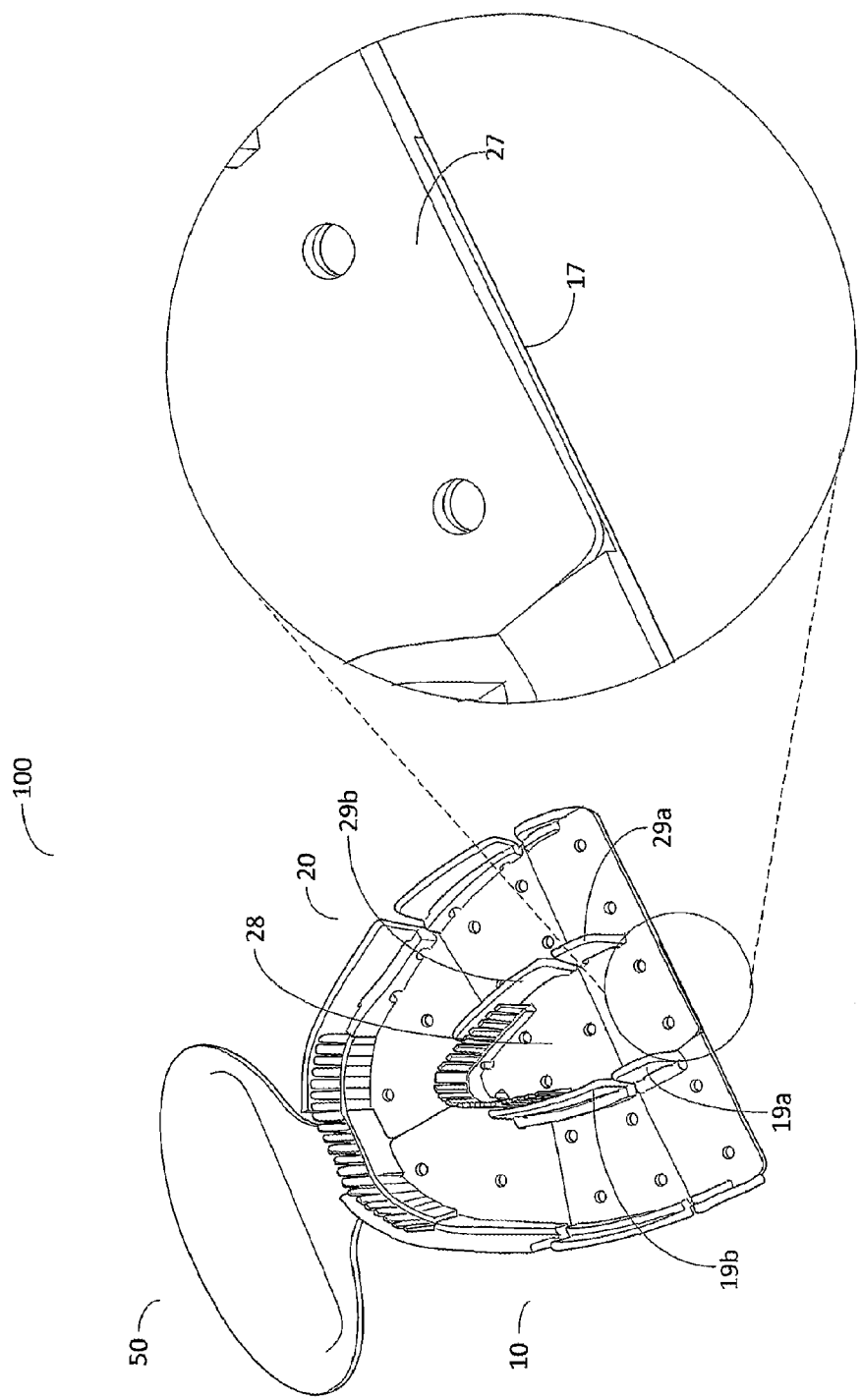
FIG. 6 is an un-adjusted view of an exemplary embodiment of dental impression tray with zoom for tongue component

FIG. 6 is an un-adjusted view of an exemplary embodiment of dual arch adjustable dental impression tray 100 with zoom view for tongue plate breakaway members. First rigid opposing half-plate 10 and second rigid opposing half-plate 20 are attached to center plate 50 and movable in a lateral direction to accommodate a wider mouth. First rigid opposing plate 10 includes rear tongue plate breakaway member 17 and forward tongue plate breakaway member 18 (not shown) which are defined by seams and may be removed to accommodate the tongue. Similarly, in the embodiment shown, second rigid opposing half-plate 20 includes rear and forward tongue plate breakaway members 27 and 28. In the embodiment shown, first and second rigid opposing half-plates 10 and 20 further include rear and forward inner-bite guard members 19a, 19b, 29a and 29b which create a barrier between the teeth receiving channel of the impression tray and the user's tongue. In the embodiment shown, rear tongue plate breakaway member 17 and forward tongue plate breakaway member 18 (not shown) overlap with rear tongue plate breakaway member 27 and forward tongue plate breakaway member 28, respectively.

Figure 7:
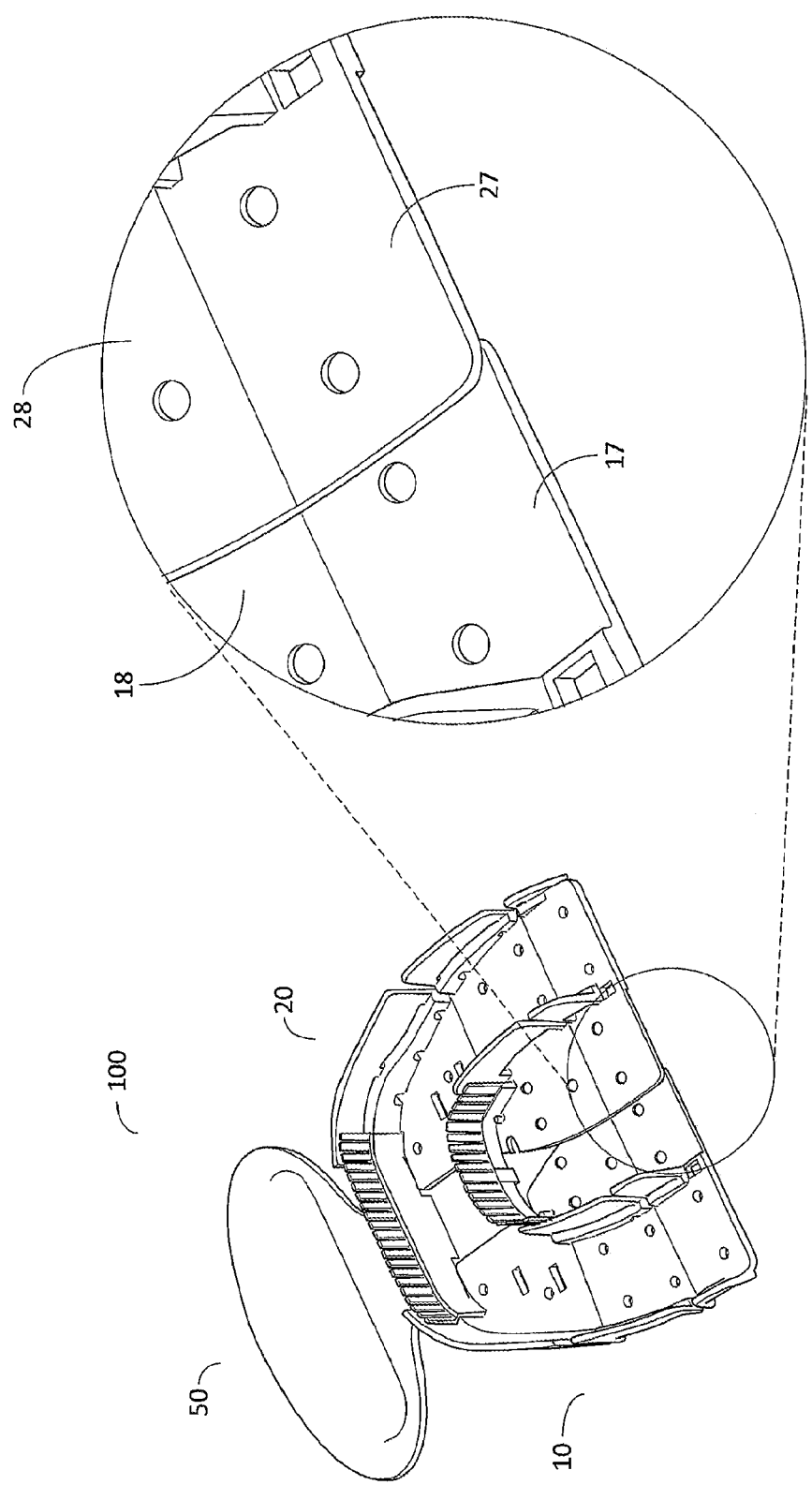
FIG. 7 is a fully adjusted view of an exemplary embodiment of dual arch dental impression tray with zoom for tongue component

FIG. 7 is a fully adjusted view of an exemplary embodiment of dual arch dental impression tray 100 with zoom for tongue component. In the embodiment shown, dental impression tray 100 is in a wider or open position. First rigid opposing half-plate 10 has rear tongue plate breakaway member 17 and forward tongue plate breakaway member which are overlapping rear tongue plate breakaway member 27 and forward tongue plate breakaway member 28. Rear and forward tongue plate breakaway members overlap each other and can be removed to accommodate the tongue of a user when using dental impression tray for lower arch impressions.

Figure 8A:
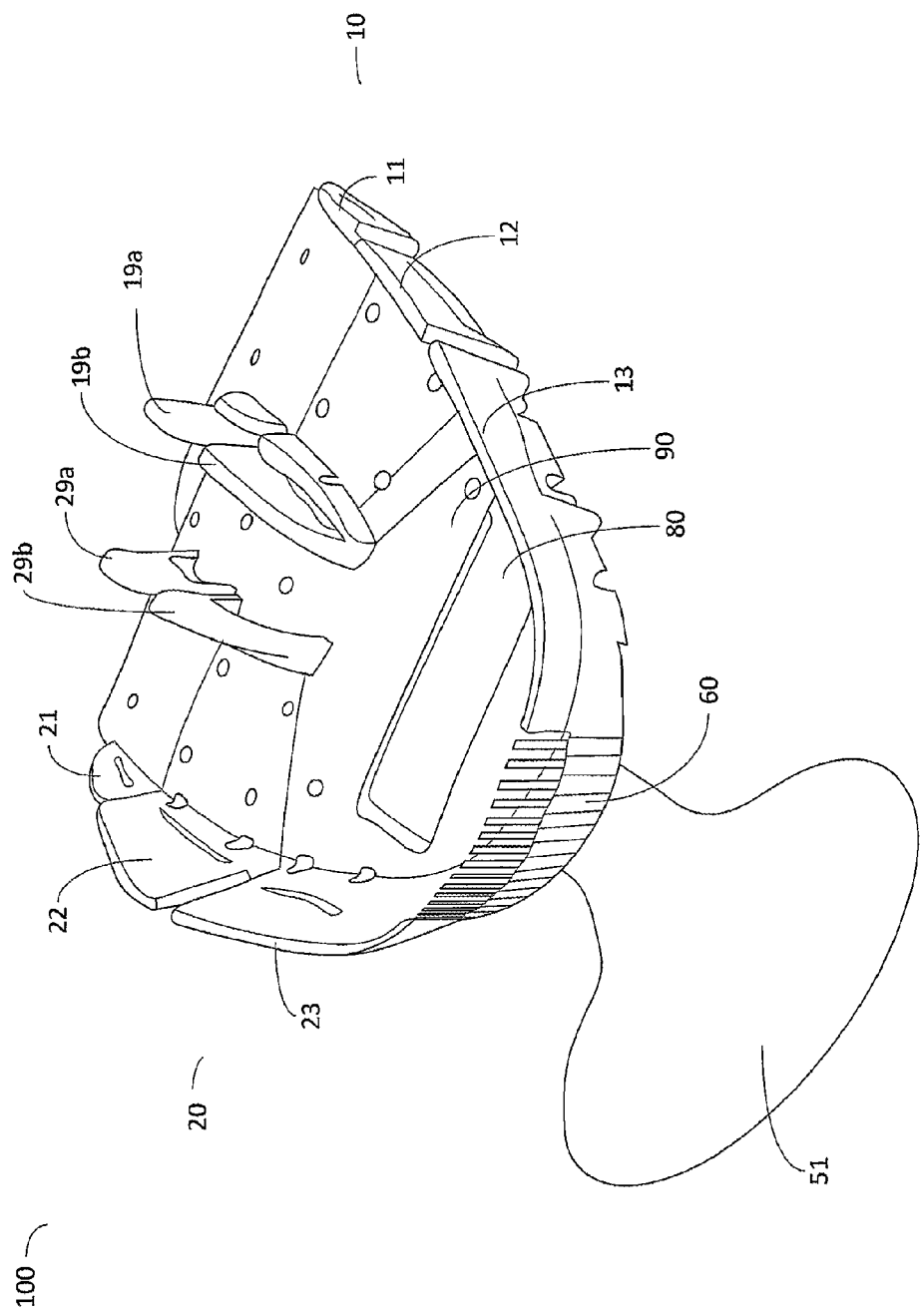
FIG. 8*a* is a top perspective view of an exemplary embodiment of a dual arch dental impression tray comprised of two opposing rigid plates in the closed position.

FIG. 8a is a top perspective view of an exemplary embodiment of a dual arch dental impression tray comprised of two opposing rigid half-plates in the closed position. Dual arch dental impression tray 100 is comprised of first rigid opposing half-plate 10 and second rigid opposing half-plate 20. In the embodiment shown, first rigid opposing half-plate 10 has rear detachable outer-bite guard member 11, middle detachable outer-bite guard member 12, and frontal detachable outer-bite guard member 13. Similarly, in the embodiment shown, second rigid opposing half-plate 20 has rear detachable outer-bite guard member 21, middle detachable outer-bite guard member 22, and frontal detachable outer-bite guard member 23. In other embodiments, outer-bite guard members may be comprised of more or fewer individual detachable sections. Detachable outer-bite guard members may be removed to accommodate a mouth which has a lower gum line. In the embodiment shown, detachable outer-bite guard member 11, 12, 13, 21, 22, and 23 include seams, which create a breaking plane, and therefore the top section of detachable outer-bite guard member may be broken off and removed to accommodate different shaped mouths.

In the embodiment shown, first rigid opposing plate 10 has securing flap 80 and second rigid opposing half-plate 20 has securing flap 90. Securing flap 80 overlaps the top of plane surface 26, while securing structure 90 overlaps the top of plane surface 16. As shown in the embodiments, the two securing flaps interlock thus creating a laterally adjustable dental impression tray.

In the embodiment shown, front flexible flap member 60 is attached to first rigid opposing half-plate 10 and extends around the front of frontal detachable outer-bite guard member 23 and will prevent impression material from escaping the dental tray as a user bites into the impression tray. In the embodiment shown, front flexible flap member 60 maintains a constant arc as first half-plate 10 and second half-plate 20 are laterally separated. In the embodiment shown, dental impression tray 100 further includes a gripping member 51 which extends from the front section of rigid opposing half-plate 10. In other embodiments, gripping member 51 maybe attached to second rigid plate, or may be its own component. In the embodiment shown, gripping member 51 is a flat oval shaped component which is used to hold dental impression tray 100 and may also be used to receive identification or advertising indicia.

Figure 8B:
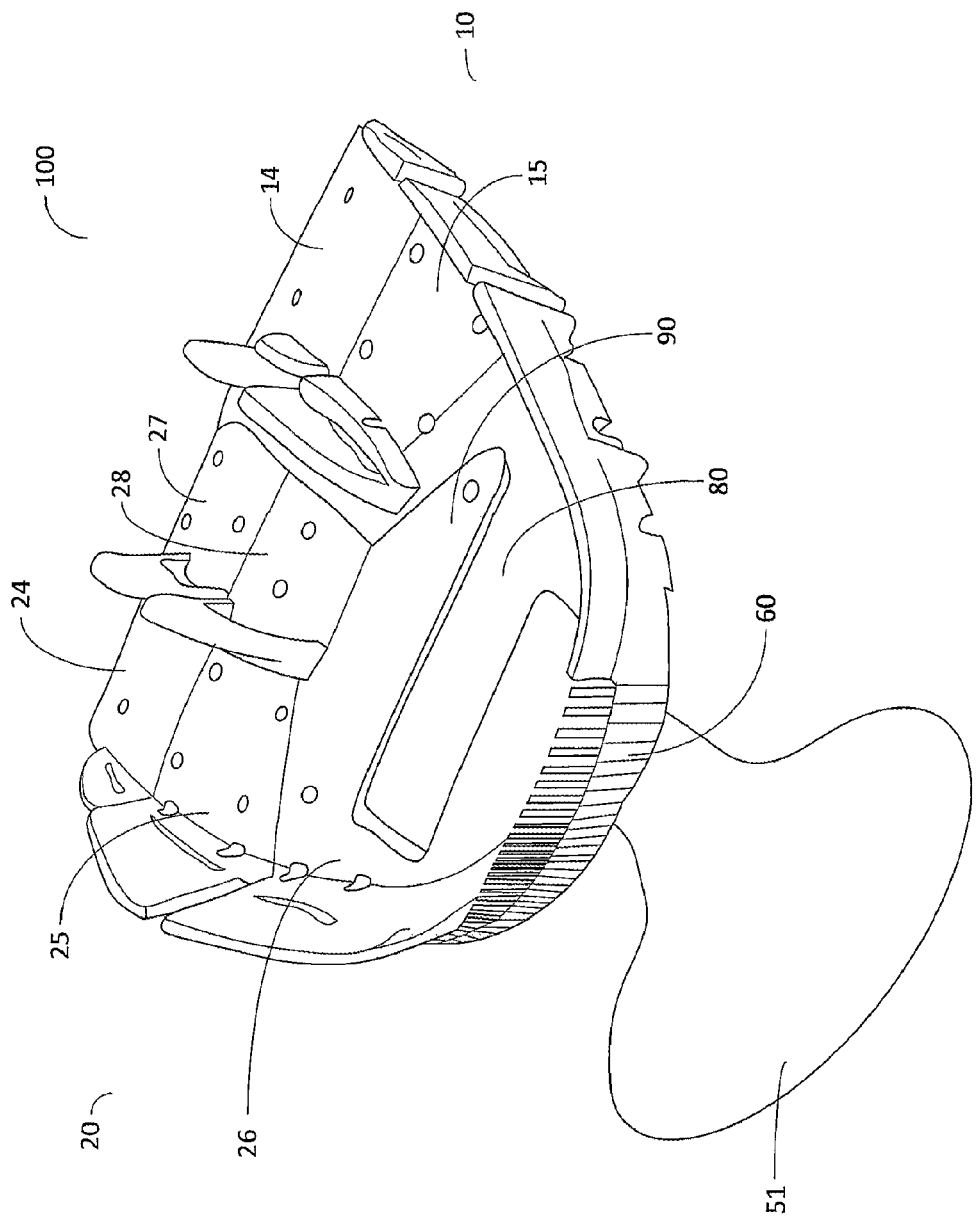
FIG. 8*b* is a top perspective view of an exemplary embodiment of a dual arch dental impression tray comprised of two opposing rigid plates in the open position.

FIG. 8b illustrates an exemplary embodiment of dental impression tray 100 with two rigid opposing half-plates 10 and 20 in a wider or more open position. As illustrated in the embodiment shown, a user may pull the two interlocking rigid half-plates apart to accommodate a wider mouth. In the embodiment shown, first half-plate 10 includes flexible flap member 60 which extends out from detachable outer-bite guard member 13 and overlaps with detachable outer-bite guard member 23. In the embodiment shown, flexible flap member 60 creates consistent arch as first half-plate 10 and second half-plate 20 are laterally separated. In other embodiments, flexible arch flap 61 maybe attached to first plate 10, or may be attached to neither plate.

What is claimed is:

1. A dental impression tray apparatus comprised of:
   a first rigid opposing half-plate and a second rigid opposing half-plate, each of said rigid opposing half-plates having a base member and at least three detachable outer-bite guard members positioned parallel to at least two detachable inner-bite guard members;
   at least one flexible flap member spanning between said detachable outer-bite guard members on each of said first rigid opposing half-plate and a second rigid opposing half-plate;
   a gripping member;
   wherein said first rigid opposing half-plate and said second rigid opposing half-plate combine to form a single universal upper palate and lower arch conforming plate;
   wherein the base member of said first rigid opposing half-plate and said second rigid opposing half-plate have a series seams located between said detachable outer-bite guard members and said detachable inner-bite guard members; and
   wherein said detachable inner bite-guard members of said first rigid opposing half-plate and a second rigid opposing half-plate further include at least two tongue plate breakaway members.

2. The apparatus of claim 1, wherein said at least one flexible flap member further includes a plurality of breakaway cylindrical components.

3. The apparatus of claim 1, further including two parallel flexible flap members each comprised of a plurality of breakaway cylindrical components.

4. The apparatus of claim 3, wherein said plurality of breakaway cylindrical components may be removed to accommodate a user's frenum.

5. The apparatus of claim 1, further including at least one interlocking track support center plate with at least two track members.

6. The apparatus of claim 5, wherein said at least one interlocking track support center plate further includes a peninsula shaped support structure.

7. The apparatus of claim 5, wherein said first rigid opposing half-plate and said second rigid opposing half-plate further include at least two track support members adapted to receive track members.

8. The apparatus of claim 5, wherein said at least one flexible flap member is perpendicular to and fixedly attached to said interlocking track support center plate.

9. The apparatus of claim 5, wherein said first rigid opposing half-plate and said second rigid opposing half-plate are secured to said interlocking track support center plate by a securing structure selected from a group consisting of a ball and detent structure, interlocking tab members, flaps, snaps, slicks, contoured interlocking components, and other pressure components.

10. The apparatus of claim 5, wherein said flat oval shaped gripping member is fixedly attached to said interlocking track support center plate.

11. The apparatus of claim 1, wherein said first rigid opposing half-plate and said second rigid opposing half-plate have a plurality of adherence apertures throughout said base members.

12. The apparatus of claim 1, wherein said at least three detachable outer-bite guard members are separated by a V-shaped space.

13. The apparatus of claim 1, wherein said first rigid opposing half-plate and said second rigid opposing half-plate have two tongue plate breakaway members.

14. The apparatus of claim 1, wherein said first rigid opposing half-plate is positioned relative to said second rigid opposing half-plate so that said at least one tongue plate breakaway member of said first rigid opposing half-plate is beneath said tongue plate breakaway member of said second rigid opposing half-plate.

15. The apparatus of claim 1, wherein said flat oval shaped gripping member is fixedly attached to said first rigid opposing half-plate.

16. The apparatus of claim 1, wherein said flat oval shaped gripping member is fixedly attached to said second rigid opposing half-plate.

17. The apparatus of claim 1, wherein said flat oval shaped gripping member is further adapted to receive identification indicia on at least one surface of said flat oval shaped gripping member.

18. The apparatus of claim 1, wherein each of said at least three detachable outer-bit guard members and each of said at least two detachable inner-bite guard members further include seams.

19. The apparatus of claim 1, further including a second flexible flap member which spans between one of said at least two detachable inner-bite guard members on each of said first rigid opposing half-plate and a second rigid opposing half-plate.

20. The apparatus of claim 1, wherein said at least one flexible flap member is fixedly attached to one of said at least three detachable outer-bite guard members on said first rigid opposing half-plate.

* * * * *